US012779246B2

(12) United States Patent
Li

(10) Patent No.: US 12,779,246 B2
(45) Date of Patent: Nov. 3, 2026

(54) METHOD AND APPARATUS FOR DETERMINING RADIOTHERAPY DOSE, DEVICE, AND STORAGE MEDIUM

(71) Applicants: OUR UNITED CORPORATION, Xi'an (CN); SHENZHEN OUR NEW MEDICAL TECHNOLOGIES DEVELOPMENT CO., LTD., Shenzhen (CN)

(72) Inventor: Bo Li, Xi'an (CN)

(73) Assignees: OUR UNITED CORPORATION, Xi'an (CN); SHENZHEN OUR NEW MEDICAL TECHNOLOGIES DEVELOPMENT CO., LTD., Shenzhen (CN)

( * ) Notice: Subject to any disclaimer, the term of this patent is extended or adjusted under 35 U.S.C. 154(b) by 189 days.

(21) Appl. No.: 18/725,641

(22) PCT Filed: Dec. 31, 2021

(86) PCT No.: PCT/CN2021/143835
§ 371 (c)(1),
(2) Date: Jun. 28, 2024

(87) PCT Pub. No.: WO2023/123420
PCT Pub. Date: Jul. 6, 2023

(65) Prior Publication Data

US 2025/0058146 A1 Feb. 20, 2025

(51) Int. Cl.
*A61N 5/10* (2006.01)
*G06T 17/20* (2006.01)
(Continued)

(52) U.S. Cl.
CPC ............ *A61N 5/1031* (2013.01); *G06T 17/20* (2013.01); *G16H 20/40* (2018.01); *G16H 50/50* (2018.01); *A61N 2005/1034* (2013.01)

(58) Field of Classification Search
CPC ....... A61N 5/1031; G16H 20/40; G16H 50/50
See application file for complete search history.

(56) References Cited

U.S. PATENT DOCUMENTS 6,148,272 A 11/2000 Bergstrom et al.
6,285,969 B1 * 9/2001 Svatos ................ A61N 5/1031 703/2
(Continued)

FOREIGN PATENT DOCUMENTS

CN 105979873 A 9/2016
CN 110504016 A 11/2019
(Continued)

OTHER PUBLICATIONS

International Search Report of the International Searching Authority for State Intellectual Property Office of the People's Republic of China in PCT application No. PCT/CN2021/143835 issued on Sep. 7, 2022, which is an international application to which this application claims priority.
(Continued)

*Primary Examiner* — Hugh Maupin
(74) *Attorney, Agent, or Firm* — Kolitch Romano Dascenzo Gates LLP

(57) ABSTRACT

Provides is a method for determining a radiotherapy dose. The method includes: acquiring a plurality of voxels by performing a three-dimensional meshing on a simulation region; acquiring simulation results of a plurality of particles by performing a parallel Monte Carlo simulation on the plurality of particles sampled within the simulation region; and determining a deposition dose for each of the plurality of voxels based on the simulation results of the plurality of particles.

17 Claims, 4 Drawing Sheets

(51) Int. Cl.

| | |
|---|---|
| ***G16H 20/40*** | (2018.01) |
| ***G16H 50/50*** | (2018.01) |

(56) References Cited

U.S. PATENT DOCUMENTS

| | | | | |
|---|---|---|---|---|
| 2004/0125103 | A1* | 7/2004 | Kaufman | G06T 15/08 345/419 |
| 2007/0071169 | A1* | 3/2007 | Yeo | A61N 5/1031 378/65 |
| 2008/0243452 | A1* | 10/2008 | Bowers | G06F 9/30 703/2 |
| 2011/0051893 | A1* | 3/2011 | McNutt | A61N 5/1031 600/407 |
| 2013/0030762 | A1* | 1/2013 | Mercier | A61N 5/1031 702/179 |
| 2015/0154374 | A1 | 6/2015 | Hissoiny | |
| 2022/0362582 | A1* | 11/2022 | Tilly | A61N 5/1037 |

FOREIGN PATENT DOCUMENTS

| | | | |
|---|---|---|---|
| CN | 110556176 | A | 12/2019 |
| CN | 112349383 | A | 2/2021 |

OTHER PUBLICATIONS

Schubert, Erich et al., Numerically stable parallel computation of (co-)variance, In Proceedings of the 30th International Conference on Scientific and Statistical Database Management (SSDBM '18), Association for Computing Machinery, New York, NY, USA, Article 10, pp. 1-12, Jul. 9, 2018, https://doi.org/10.1145/3221269.3223036.

* cited by examiner

METHOD AND APPARATUS FOR DETERMINING RADIOTHERAPY DOSE, DEVICE, AND STORAGE MEDIUM

CROSS-REFERENCE TO RELATED APPLICATION

This application is a U.S. national phase application based on PCT/CN2021/143835, filed on Dec. 31, 2021, the content of which is incorporated herein by reference in its entirety.

TECHNICAL FIELD

The present disclosure relates to the field of medical information technology, and in particular, relates to a method for determining a radiotherapy dose, an apparatus, a device, and a non-transitory storage medium.

BACKGROUND

To ensure the accuracy of radiotherapy, the dose distribution of a target object can be acquired by performing a radiotherapy simulation before the treatment of the target object, such that the dose distribution can be used as a reference to develop a matching radiotherapy plan for the target object.

SUMMARY

Embodiments of the present disclosure provide a method for determining a radiotherapy dose, an apparatus, a device, and a non-transitory storage medium.

According to some embodiments of the present disclosure, a method for determining a radiotherapy dose is provided, including:

acquiring a plurality of voxels by performing a three-dimensional meshing on a simulation region;

acquiring simulation results of a plurality of particles by performing a parallel Monte Carlo simulation on the plurality of particles sampled within the simulation region; and determining a deposition dose for each of the plurality of voxels based on the simulation results.

In some embodiments, acquiring the simulation results of the plurality of particles by performing the parallel Monte Carlo simulation on the plurality of particles sampled within the simulation region includes:

determining, based on each of the plurality of particles, an incident angle and incident voxels of the corresponding particle entering the simulation region; and acquiring, based on the incident angle and the incident voxels, the simulation result by allocating cache spaces for a portion of the voxels within the simulation region and performing a Monte Carlo simulation until the particle penetrates the simulation region, wherein the cache space is configured to store deposition energy of the particle in a corresponding voxel.

In some embodiments, acquiring, based on the incident angle and the incident voxels, the simulation result by allocating the cache spaces for the portion of the voxels within the simulation region and performing the Monte Carlo simulation until the particle penetrates the simulation region includes:

sequentially determining, based on the incident angle and the incident voxels, a deposition region corresponding to each layer of voxels of the particle in the simulation region;

allocating a corresponding cache space for each voxel in the deposition region corresponding to each layer of voxels;

performing the Monte Carlo simulation based on the incident angle and the incident voxels until the particle penetrates the simulation region and storing the deposition energy of the particle in the corresponding voxel into the cache space; and acquiring the simulation result by transferring data in the cache space to a shared storage space.

In some embodiments, sequentially determining, based on the incident angle and the incident voxels, the deposition region corresponding to each layer of voxels of the particle in the simulation region, and allocating the corresponding cache space for each voxel in the deposition region corresponding to each layer of voxels include:

determining, based on the incident angle, the incident voxels and voxels within a predetermined periphery of the incident voxels in a first layer of voxels as a first layer of deposition region corresponding to the particle in the first layer of voxels;

allocating a corresponding cache space for each voxel in the first layer of deposition region to store deposition energy of each voxel in the first layer of deposition region;

determining, in the case that the particle enters a next layer of voxels, voxels within a region of the next layer of voxels corresponding to the first layer of deposition region and voxels within a predetermined periphery thereof as a second layer of deposition region corresponding to the particle in the next layer of voxels;

allocating a corresponding cache space for each voxel in the second layer of deposition region to store deposition energy of each voxel in the second layer of deposition region; and sequentially determining a deposition region when the particle entering each layer of voxels and allocating a corresponding cache space to store deposition energy of each voxel in a corresponding deposition region.

In some embodiments, acquiring the simulation result by transferring the data in the cache space to the shared storage space includes:

releasing, in response to the particle entering a nth layer of the simulation region, a cache space corresponding to each voxel in a deposition region corresponding to each layer of voxels before a mth layer, wherein m is a positive integer less than n; and transferring data stored in the released cache space to the shared storage space.

In some embodiments, the method further includes:

calculating an uncertainty of the parallel Monte Carlo simulation according to deposition energy of an Nth particle in the shared storage space, wherein N is equal to a quantity of the plurality of particles.

In some embodiments, calculating the uncertainty of the parallel Monte Carlo simulation according to the deposition energy of the Nth particle in the shared memory space includes:

calculating the uncertainty of the parallel Monte Carlo simulation according to deposition energy of the Nth particle in a single voxel and an energy variance of the Nth particle in a single voxel;

wherein the deposition energy of the Nth particle in the single voxel is an average deposition dose of the Nth particle in corresponding voxels, and the energy variance of the Nth particle in the single voxel is a sum of a variance of the deposition energy of the Nth particle in corresponding voxels and the average deposition energy.

According to some embodiments of the present disclosure, an apparatus for determining a radiotherapy dose is provided, including:

- a meshing module, configured to acquire a plurality of voxels by performing a three-dimensional meshing on a simulation region;
- a simulating module, configured to acquire simulation results of a plurality of particles by performing a parallel Monte Carlo simulation on the plurality of particles sampled within the simulation region; and
- a determining module, configured to determine a deposition dose for each of the plurality of voxels based on the simulation results.

According to some embodiments of the present disclosure, a computer device is provided, including: a memory and a processor, wherein the memory stores one or more computer programs executable by the processor, and the processor, when loading and executing the one or more computer programs, is caused to perform the method for determining the radiotherapy dose as described in any of the above embodiments.

According to some embodiments of the present disclosure, a non-transitory computer-readable storage medium is provided, storing one or more computer programs, wherein the one or more computer programs, when loaded and executed by a processor, cause the processor to perform the method for determining the radiotherapy dose as described in any of the above embodiments.

BRIEF DESCRIPTION OF THE DRAWINGS

To describe the technical solutions in the embodiments of the present disclosure more clearly, the following briefly introduces the accompanying drawings required for describing the embodiments. It should be understood that the accompanying drawings in the following description show merely some embodiments of the present disclosure, and therefore should not be regarded as a limitation of the scope, and a person of ordinary skill in the art may still derive other drawings from these accompanying drawings without creative efforts.

DETAILED DESCRIPTION

Figure 1:
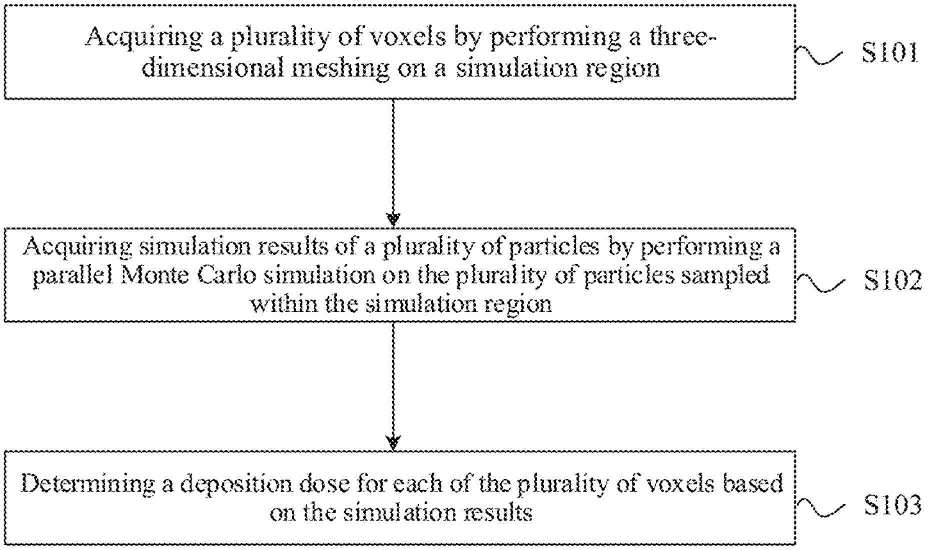
FIG. 1 is a flowchart of a method for determining a radiotherapy dose according to some embodiments of the present disclosure.

For clearer descriptions of the objectives, technical solutions, and advantages of the present disclosure, embodiments of the present disclosure are clearly and completely described hereinafter with reference to the accompanying drawing, and obviously, the described embodiments are a portion of the embodiments of the present disclosure and not all of the embodiments.

In the description of the present disclosure, it is to be understood that the terms "first" and "second" are used for descriptive purposes only, and are not to be construed as indicating or implying relative importance or implicitly specifying the number of indicated technical features. Therefore, features defined as "first" and "second" may expressly or implicitly include one or more of the described features. In the description of the present disclosure, "a plurality of" means two or more unless specifically defined otherwise.

In the present disclosure, the term "exemplary" is used to mean "serving as an example, instance, or illustration". Any embodiment described herein as "exemplary" is not necessarily to be construed as preferred or advantageous over other embodiments. The following description is presented to enable any person skilled in the art to realize and use the present disclosure. In the following description, details are set forth for purposes of explanation. It will be apparent to one of ordinary skill in the art that the present disclosure may be practiced without these specific details. In other examples, well-known structures and processes are not set forth in detail to avoid making the description of the present disclosure obscure with unnecessary details. Thus, the present disclosure is not intended to be limited to the embodiments shown, but is consistent with the widest scope consistent with the principles and features disclosed herein.

In related art, a serial Monte Carlo simulation is mostly used in the process of radiotherapy simulation. The serial Monte Carlo simulation indicates simulating a plurality of sampled particles sequentially, i.e., when the simulation of one particle is completed, the simulation of the next particle can be performed.

The time required for the serial Monte Carlo simulation is relatively long, such that the time for developing a treatment plan is correspondingly prolonged, and the time of the entire treatment process is increased. Embodiments of the present disclosure provide a method for determining a radiotherapy dose, which can shorten the entire duration of a radiotherapy simulation process, shorten the time for developing a treatment plan, and thus shorten the time of the entire treatment process.

Before describing a method for determining a radiotherapy dose according to the embodiments of the present disclosure, the technical terms involved in the embodiments of the present disclosure are explained below.

Monte Carlo simulation: as the most accurate algorithm in the radiotherapy field, it can sample the emitted particles of the source model by using a preset probability distribution model, and then simulate the movement process of the particles within the to-be-simulated region in accordance with the statistical law of the movement of the microscopic particles to acquire the distribution of the radiation dose of the sampled particles within the to-be-simulated region. The parallel Monte Carlo simulation is performed by simulating the movement process of a plurality particles simultaneously.

Compared with the process of performing radiotherapy simulation by adopting a serial Monte Carlo simulation method in the conventional technology, the embodiments of the present disclosure provide a method for performing radiotherapy simulation by adopting a parallel Monte Carlo simulation method, so as to determine a plurality of possible implementations of a radiotherapy plan.

The device performing the method for determining the radiotherapy dose according to some embodiments of the present disclosure can be a computer device installed with a radiotherapy dose determination application, and the computer device can perform a corresponding method for determining the radiotherapy dose by running the radiotherapy dose determination application. The radiotherapy dose determination application is a sub-functional module of a treatment plan system (TPS), which is also referred to as a Monte Carlo calculation module.

The method for determining the radiotherapy dose according to some embodiments of the present disclosure is first explained and illustrated by way of example below in conjunction with a plurality of examples. FIG. 1 is a flowchart of the method for determining the radiotherapy dose according to some embodiments of the present disclosure. As shown in FIG. 1, the method for determining the radiotherapy dose includes:

S101, a plurality of voxels are acquired by performing a three-dimensional meshing on a simulation region.

The simulation region, also referred to as the calculation region, is a predetermined three-dimensional region of a target object, and the target object is a to-be-treated object or a predetermined mold object. The simulation region is actually a three-dimensional region, thus meshing the simulation region is performed on the three-dimensional space. The three-dimensional meshing is performed on the simulation region based on the size of a predetermined single voxel to acquire the plurality of voxels, such that the simulation region has a, b, and c voxels on each of the three axes in a predetermined three-dimensional coordinate system. The predetermined three-dimensional coordinate system is, for example, an xyz coordinate system, and the three coordinate axes are an x coordinate axis, a y coordinate axis, and a z coordinate axis respectively.

S102, simulation results of a plurality of particles are acquired by performing a parallel Monte Carlo simulation on the plurality of particles sampled within the simulation region.

Before performing the parallel Monte Carlo simulation, the emitted particles of the emission source module are sampled based on a predetermined probability distribution model to acquire the sampled plurality of particles. The predetermined probability distribution model is, for example, a random probability distribution model, or other probability distribution model, which is not limited in the embodiments of the present disclosure. In the case of acquiring the sampled plurality of particles, the parallel Monte Carlo module is performed on the plurality of particles within the simulation region, and in the process of performing a Monte Carlo simulation on each particle, the motion of the corresponding particle within the simulation region is simulated. In the process of the motion simulation, the deposition energy of the corresponding particle in the voxels is calculated, such that the simulation result of the corresponding particle is acquired.

S103, a deposition dose for each of the plurality of voxels is determined based on the simulation results.

The simulation result of each particle includes the deposition energy of the corresponding particle in the voxels, and then, in some embodiments, the deposition dose for each voxel is determined based on the simulation results of the plurality of particles, and thus the radiation dose distribution of each voxel in the simulation region is acquired.

Exemplarily, in the process of determining the deposition dose for each of the plurality of voxels based on the simulation results of the plurality of particles, the deposition energy of the plurality of particles in the same voxel is combined to acquire the deposition dose for the corresponding voxel.

The method for determining the radiotherapy dose according to some embodiments of the present disclosure acquires a plurality of voxels by performing a three-dimensional meshing on a simulation region, and acquires simulation results of the plurality of particles by performing a parallel Monte Carlo simulation on the plurality of particles sampled within the simulation region, and then determines a deposition dose for each of the plurality of voxels based on the simulation results. In other words, the method for determining the radiotherapy dose according to the embodiments of the present disclosure is actually a method for determining the radiotherapy dose by the parallel Monte Carlo simulation method. The Monte Carlo simulation method for a plurality of particles is executed in parallel, effectively shortening the time for determining the radiotherapy dose during the entire radiotherapy simulation process, improving the efficiency of the Monte Carlo simulation, and shortening the time for developing a treatment plan, and thus shortening the time for the entire treatment process.

Figure 2:
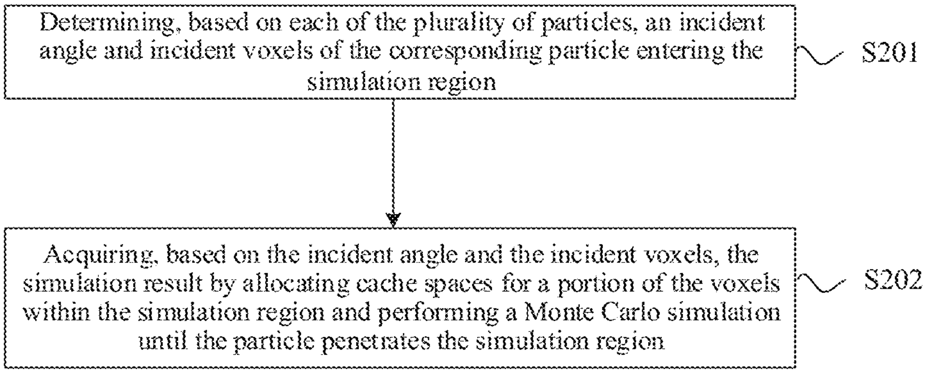
FIG. 2 is a flowchart of a parallel Monte Carlo simulation method in a method for determining a radiotherapy dose according to some embodiments of the present disclosure.

Based on the method for determining the radiotherapy dose according to the above embodiments of the present disclosure, the present disclosure also provides, by a plurality of embodiments, possible ways for realizing the parallel Monte Carlo simulation for a plurality of particles. FIG. 2 is a flowchart of a parallel Monte Carlo simulation method in a method for determining a radiotherapy dose according to some embodiments of the present disclosure. As shown in FIG. 2, acquiring the simulation results of the plurality of particles by performing the parallel Monte Carlo simulation on the plurality of particles sampled within the simulation region as described in above S102 includes:

S201, based on each of the plurality of particles, an incident angle and incident voxels of the corresponding particle entering the simulation region are determined.

In the case that a plurality of particles are sampled, that is, an exit angle of each of the sampled particles from the emission source model is determined. Therefore, for each of the particles, the incident angle at which the corresponding particle enters the simulation region as well as the incident voxels are determined based on the exit angle of the corresponding particle determined in the sampling process, and a position of the simulation region relative to the emission source model. The incident voxels are the voxels that the particle passes through on its trajectory within the simulation region. The incident angle is the angle at which the particles enter the simulation region.

For the convenience of description, assuming that the incident direction corresponding to the incident angle of the particle is the negative direction of the z-coordinate axis, then it can be determined that the first voxel met by the particle entering the simulation region is the cth voxel along the positive direction of the z-coordinate axis. Therefore, it can be determined that the incident voxels include the first met voxel v (i, j, c) and other incident voxels upon penetration from the first met voxel.

S202, based on the incident angle and the incident voxels, the simulation result is acquired by allocating cache spaces for a portion of the voxels within the simulation region and a Monte Carlo simulation is performed until the particle penetrates the simulation region.

The cache space is configured to store deposition energy of the particle in a corresponding voxel.

In the specific implementation, based on the above-determined incident angle and the incident voxels of the particle, the Monte Carlo simulation is performed. In the simulation process, the corresponding cache spaces are allocated to a portion of the voxels within the simulation region until the particle movement passes through the simulation region, the Monte Carlo simulation of the particle is completed, and the simulation result is acquired. The portion of voxels in the simulation process are voxels associated with the trajectory of the particle within the simulation region, for example, includes voxels through which the trajectory of the particle in the simulation region traversed, and voxels within a predetermined range around the trajectory of the particle in the simulation region, and the like.

Allocating the cache spaces for the portion of the voxels within the simulation region indicates allocating one cache space for each voxel in the portion of the voxels within the simulation region for storing the deposition energy of the particle in the corresponding voxel. In some possible implementations, the size of each cache space may be, for example, a predetermined number of bytes of cache region, such as a four-byte floating-point buffer.

Assuming that the portion of the voxels within the simulation region include k voxels, k cache spaces can be allocated to store the deposition energy of the particle in the k voxels, respectively.

The method for determining the radiotherapy dose according to some embodiments of the present disclosure can determine the incident angle and the incident voxels of each of the particles entering the simulation region, and based on the incident angle and the incident voxels, allocate cache spaces for a portion of the voxels within the simulation region, and perform the Monte Carlo simulation until the particle penetrates out of the simulation region to acquire the simulation result, and the allocated cache space is configured to store deposition energy of the particle in the corresponding voxel during the simulation process. In other words, in the process of performing parallel Monte Carlo simulation for determining the radiotherapy dose, the Monte Carlo simulation for each particle does not allocate corresponding cache spaces for all voxels within the simulation region, but only allocates corresponding cache spaces for a portion of the voxels associated with the particle within the simulation region to store the deposition energy of the particle in the corresponding voxel, such that the memory resources required for the Monte Carlo simulation for each particle in the parallel Monte Carlo simulation are effectively reduced, thereby ensuring the parallel efficiency of the Monte Carlo simulation for the plurality of particles, effectively shortening the overall computation time for determining the radiotherapy dose, shortening the time for developing a treatment plan, and thus shortening the time for the entire treatment process.

Figure 3:
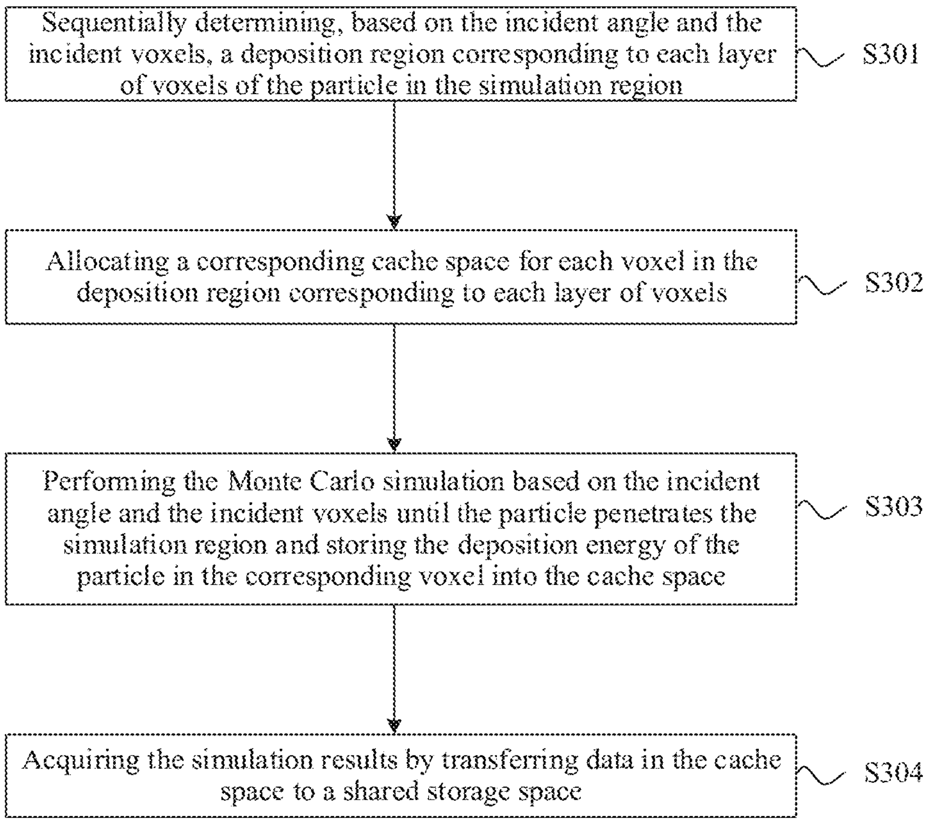
FIG. 3 is a method flowchart I of a Monte Carlo simulation process in a method for determining a radiotherapy dose according to some embodiments of the present disclosure.

Combined with the accompanying drawings, the illustration below provides a plurality of possible implementations of the method for determining the radiotherapy dose by exemplary explanatory illustrations of a plurality of examples of implementations of the Monte Carlo simulation process for a particle. FIG. 3 is a method flowchart I of a Monte Carlo simulation process in a method for determining a radiotherapy dose according to some embodiments of the present disclosure. As shown in FIG. 3, acquiring the simulation result by allocating the cache spaces for the portion of the voxels within the simulation region and performing the Monte Carlo simulation until the particle penetrates the simulation region based on the incident angle and the incident voxels in the above S202 includes:

S301, based on the incident angle and the incident voxels, a deposition region corresponding to each layer of voxels of the particle in the simulation region is sequentially determined.

In a specific implementation, based on the incident angle and the incident voxels, a motion simulation is performed on the particle within the simulation region, and then based on the result of the motion simulation, a deposition region corresponding to each layer of voxels of the particle in the simulation region is sequentially determined. The deposition region refers to a three-dimensional region including a plurality of voxels having deposition energy of the particle. The result of the motion simulation includes, for example, a motion trajectory of the particle within the simulation region, and a motion trajectory of a secondary particle generated in the motion of the particle within the simulation region. The motion trajectory of the particle within the simulation region is represented by a coordinate position of the voxel penetrated by the particle, and accordingly, the motion trajectory of the secondary particle within the simulation region is represented by a coordinate position of the voxel penetrated by the secondary particle.

S302, a corresponding cache space is allocated for each voxel in the deposition region corresponding to each layer of voxels.

Upon determining the deposition region corresponding to each layer of voxels, a corresponding cache space is allocated to each voxel in the deposition region corresponding to each layer of voxels, that is, one cache space is divided for each voxel in the deposition region corresponding to each layer of voxels. The quantity of voxels in the deposition regions corresponding to different layers of voxels may be different, and thus the amount of cache spaces allocated for the voxels in the deposition regions corresponding to different layers of voxels is different.

The quantity of voxels in the deposition region corresponding to each layer of voxels is a value determined based on at least one parameter such as the density of the voxels within the simulation region, the type of medium, the type of particles, the energy of the particle entering each layer of voxels, the incident angle, the degree of freedom corresponding to the type of medium, and the like, in combination with the physical motion law of the particle. In other words, in the case that the particle moves in each layer of voxels, there is no need to allocate cache spaces for all the voxels in each layer of voxels, but rather for a portion of the voxels associated with the particle's law of motion in each layer of voxels, that is, the voxels in the deposition region corresponding to each layer of voxels, which greatly reduces the amount of cache spaces required for a particle when moving within each voxel layer in the simulation region.

Since in the simulation region, the densities of different layers of voxels, the types of media, the energy of a particle entering the voxels in one layer, the incident angle, and the free ranges in the media may all be different, the voxels in the deposition region corresponding to different layers of voxels in the simulation region are different.

Assuming that the deposition region corresponding to the first voxel layer includes k1 voxels, and k1 cache spaces are allocated for the k1 voxels in the deposition region corresponding to the first voxel layer to store the deposition energy of the particle in the k1 voxels, respectively; the deposition region corresponding to the second voxel layer includes k2 voxels, and k2 cache spaces are allocated for the k2 voxels in the deposition region corresponding to the second voxel layer to store the deposition energy of the particle in the k2 voxels, respectively, and so on.

It should be noted that the allocation of the cache spaces is performed when a certain layer of voxels is entered and the corresponding deposition region corresponding to the voxels of the layer is determined, and when a new layer of voxels is not entered, the allocation of the cache spaces is not performed because the corresponding deposition region cannot be determined. The above examples are given only for the convenience of understanding the relationship between the voxels in the deposition region corresponding to each layer of voxels and the corresponding allocated cache spaces.

S303, the Monte Carlo simulation is performed based on the incident angle and the incident voxels until the particle penetrates the simulation region, and the deposition energy of the particle in the corresponding voxel is stored into the cache space.

In the case that the particle penetrates from a certain layer of voxels, it is necessary to continue the Monte Carlo simulation based on the incident angle and the incident voxels until the particle penetrates the entire simulation region. Then the Monte Carlo simulation of the particle within the simulation region is completed, and in the process of simulation, the deposition energy of the particle acquired by the simulation in the corresponding voxel in the layer of voxels is stored in the cache space of each voxel.

The cache space allocated to each voxel in the deposition region corresponding to each layer of voxels is configured to store deposition energy of a particle and/or a secondary particle of the particle in the corresponding voxel.

S304, the simulation result is acquired by transferring data in the cache space to a shared storage space.

In some embodiments, upon determining that the simulation process of the particle within the simulation region is completed, the data in the cache spaces for the corresponding particle is all transferred to the shared storage space, thereby acquiring the simulation result; alternatively, the data in some of the cache spaces is transferred to the shared storage space during the simulation process, and after the simulation process is completed, the data in the other cache spaces is transferred to the shared storage space, thereby acquiring the simulation result. The shared storage space is a shared memory space for a plurality of parallel Monte Carlo processes for a plurality of particles.

In the method according to the present embodiment, by sequentially determining a deposition region corresponding to each layer of voxels of the particle in the simulation region, allocating a corresponding cache space for each voxel in the deposition region corresponding to each layer of voxels, and performing the Monte Carlo simulation for the particle until the particle penetrates the simulation region, storing the deposition energy of the particle in the corresponding voxel into the cache space, and acquiring the simulation result by transferring data in the cache space to a shared storage space, the determination of a deposition region for each particle during the Monte Carlo simulation process, the allocation of cache space for each voxel within the deposition region, and the allocation of cache spaces for a portion of the voxels in the simulation region provide clear examples, which effectively ensures that there is no needed to allocate cache spaces for all the voxels during the Monte Carlo simulation process for each particle, and effectively reduces the amount of memory resources consumed during the Monte Carlo simulation process for each particle, such that the efficiency of parallel execution of the parallel Monte Carlo simulation process for a plurality of particles is ensured.

Figure 4:
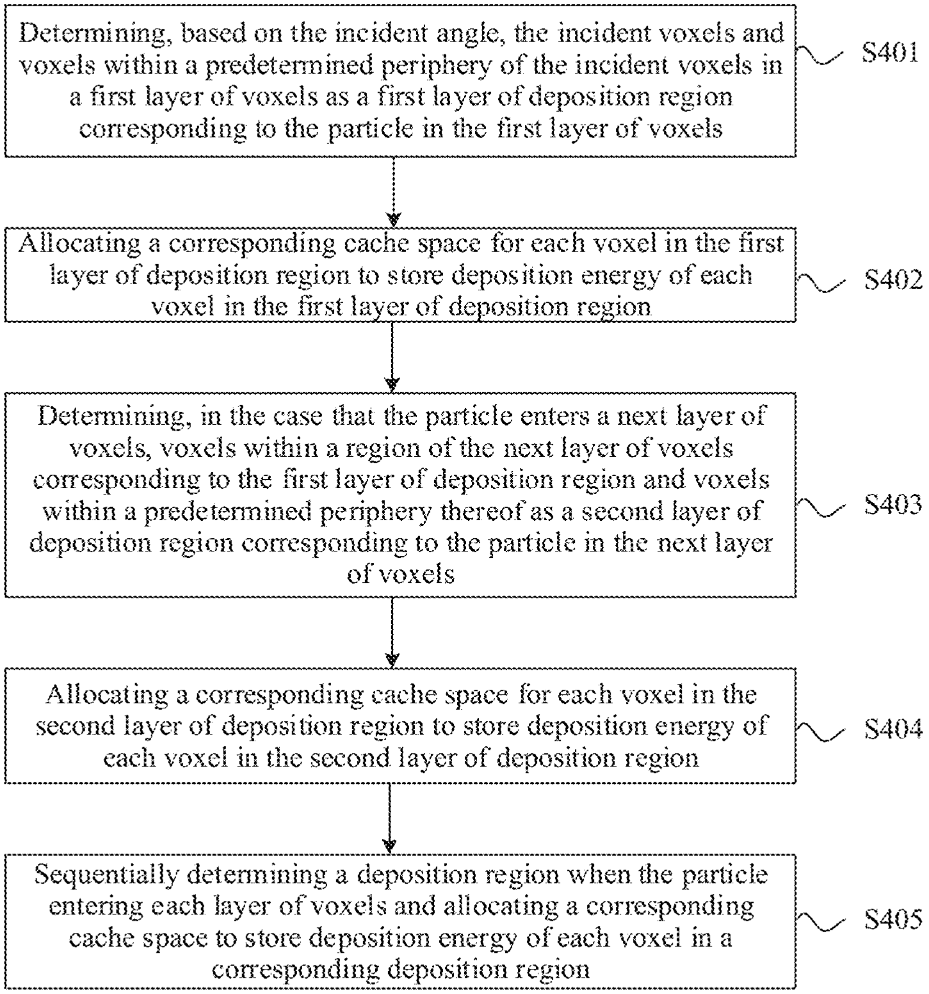
FIG. 4 is a method flowchart II of a Monte Carlo simulation process in a method for determining a radiotherapy dose according to some embodiments of the present disclosure.

Based on the solutions according to the above embodiments, the embodiments of the present disclosure also provide other possible implementations for the Monte Carlo simulation process for a particle. FIG. 4 is a method flowchart II of a Monte Carlo simulation process in a method for determining a radiotherapy dose according to some embodiments of the present disclosure. As shown in FIG. 4, sequentially determining, based on the incident angle and the incident voxels, the deposition region corresponding to each layer of voxels of the particle in the simulation region in above S301, and allocating the corresponding cache space for each voxel in the deposition region corresponding to each layer of voxels in the above S302 includes:

S401, based on the incident angle, the incident voxels and voxels within a predetermined periphery of the incident voxels in a first layer of voxels are determined as a first layer of deposition region corresponding to the particle in the first layer of voxels.

In some embodiments, the voxels within the predetermined periphery of the incident voxels in the first layer of voxels are determined based on the incident angle, and the incident voxels and the voxels within the predetermined periphery of the incident voxels are determined as the first layer of deposition region corresponding to the particle in the first layer of voxels. That is, the voxels within the first layer of deposition region include the incident voxels and the voxels within the predetermined periphery of the incident voxels, wherein the incident voxels are voxels through which a trajectory of a particle and/or a secondary particle in the first layer of voxels passes, and the voxels within the predetermined periphery of the incident voxels are voxels within a predetermined periphery of the motion trajectory of a corresponding particle in the first layer of voxels. The size of the predetermined peripheral is a three-dimensional regional range determined based on the incident angle with the incident voxels as the reference point.

S402, a corresponding cache space is allocated for each voxel in the first layer of deposition region to store deposition energy of each voxel in the first layer of deposition region.

Continuing with the above example, in the case that the incident direction corresponding to the incident angle of the particle is in the negative direction of the z-coordinate axis, and the particle enters the first voxel v (i, j, c) of the first layer of voxels, one cache space is allocated for the first voxel v to store the deposition energy of the particle within the first voxel v. In the case that the particle moves to the first adjacent voxel v (i+1, j, c) in the first layer of voxels with the z-coordinate value still being c, another cache space is allocated for the first adjacent voxel to store the deposition energy of the first adjacent voxel. In the case that the particle continues to move to the second adjacent voxel v (i+1, j+1, c) in the first layer of voxels with the z coordinate value still being c, another cache space is allocated for the second adjacent voxel to store the deposition energy of the second adjacent voxel.

Assuming that the motion trajectory of the particle in the first layer of voxels passes through k11 voxels with the z-coordinate being c, and the voxels in the predetermined periphery of the motion trajectory of the particle in the first layer with the z-coordinate being c are k12 voxels, it is determined that the deposition region corresponding to the first layer of voxel includes: k11 voxels through which the motion trajectory passes, and k12 voxels in the predetermined periphery of the motion trajectory. In this way, k1 cache spaces are allocated for the deposition region corresponding to the first layer of voxels to store the deposition energy of the k1 voxels, wherein k1=k11+k12. In this example, the first layer of voxels can be a layer of voxels with the z-coordinate being c, and the z-coordinates of each voxel in the first layer of deposition region corresponding to the first layer of voxels determined from the first layer of voxels are also c.

S403, in the case that the particle enters a next layer of voxels, voxels within a region of the next layer of voxels corresponding to the first layer of deposition region and voxels within a predetermined periphery thereof are determined as a second layer of deposition region corresponding to the particle in the next layer of voxels.

In the case that the particle enters the next layer of voxels, i.e., from the first layer of voxels with z-coordinate being c into the next layer of voxels with z-coordinate being c−1, the voxels in the motion trajectory of the particle in the next layer of voxels are determined to be the region in the next layer of voxels corresponding to the first layer of deposition region, and in conjunction with the determined voxels within the predetermined periphery of the motion trajectory of the particle, the voxels are determined as the second layer of deposition region corresponding to the particle in the next layer of voxels. The motion trajectory of the particle refers to a motion trajectory of the particle and/or a secondary particle generated by the particle. That is, the second layer of deposition region includes voxels through which the motion trajectory of the particle passes, and voxels within a predetermined periphery of the motion trajectory of the particle.

S404, a corresponding cache space is allocated for each voxel in the second layer of deposition region to store deposition energy of each voxel in the second layer of deposition region.

The specific implementation of allocating the corresponding cache space for each voxel in the second layer of deposition region is similar to the above implementation process of allocating the cache space for each voxel in the first layer of deposition region, which is not repeated herein.

In the case that the particle enters the next layer of voxels with z-coordinate being c from the first layer of voxels with z-coordinate being c, and the corresponding second layer of deposition region in the next layer of voxels with z-coordinate being c−1 includes k2 voxels, k2 voxels need to be allocated for the second layer of deposition region to store deposition energy of the k2 voxels. S405, a deposition region when the particle entering each layer of voxels is sequentially determined and a corresponding cache space is allocated, so as to store the deposition energy of each voxel in a corresponding deposition region.

Since the motion of the particle within the simulation region is continuous, the simulation of the particle is continued upon the particle penetrating from the second layer of voxels, and the deposition region when the particle entering each layer of voxels is sequentially determined until the particle penetrates the simulation region. It should be noted that the specific implementation process of determining the deposition region when the particle entering the next layer of voxels from the previous layer of voxels is similar to the implementation process of determining the deposition region when the second layer of the particle entering the second layer of voxels from the first layer of voxels described above with specific reference to the above, which is not repeated herein. During the simulation process, a corresponding cache space is allocated for the voxels in the deposition region corresponding to each layer of voxels to store the deposition energy of each of the voxels in the corresponding deposition region.

In the method according to the embodiments, by determining the corresponding deposition region of the particle in each layer of voxels, the portion of voxels needed to be allocated cache spaces in the deposition region corresponding to each layer of voxels is determined more accurate, which ensures the accurate determination of the deposition region corresponding to each layer of voxels, ensures the accuracy of the number of cache spaces allocated for the voxels in the deposition region corresponding to each layer of voxels, and effectively reduces the consumption of the number of cache spaces allocated for each particle in the simulation region during the Monte Carlo simulation process within the simulation region, thereby effectively ensuring the efficiency of the parallel execution of the parallel Monte Carlo simulation process for the plurality of particles.

Figure 5:
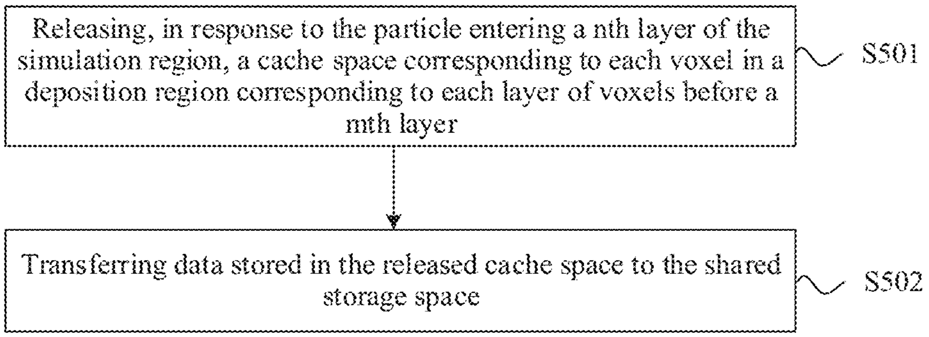
FIG. 5 is a method flowchart of data transferring in a cache space in a method for determining a radiotherapy dose according to some embodiments of the present disclosure.

Based on the solutions provided in the above embodiments, the embodiments of the present disclosure also provide a possible method for transferring the data in the cache space to the shared storage space. FIG. 5 is a method flowchart of data transferring in a cache space in a method for determining a radiotherapy dose according to some embodiments of the present disclosure. As shown in FIG. 5, acquiring the simulation result by transferring the data in the cache space to the shared storage space in the above S304 includes:

S501, in response to the particle entering a nth layer of the simulation region, a cache space corresponding to each voxel in a deposition region corresponding to each layer of voxels before a mth layer is released.

M is a positive integer less than n. Because the particle scatters or the moving direction is deflected during transmission, the particle has a small probability of entering the same voxel multiple times. To ensure the accuracy of the statistical results, the number of layers of the buffer cannot be too small, and cannot be set arbitrarily, or else the probability that the statistical results are incorrect is increased. Therefore, in the embodiments, the specific value of m is determined based on the voxel parameter of the simulation region and the attribute parameter of the particle. The voxel parameter includes at least one parameter of the density of the voxel, the type of medium in the voxel, and the degree of freedom corresponding to the type of medium, and the attribute parameter includes at least one parameter of the type of the particle, the initial energy of the particle, and the incident angle of the particle.

The method provided by the embodiments can buffer the deposition energy in the voxel at a maximal degree within an acceptable range, that is, in response to the particle entering a certain layer, the particle also generates deposition energy in a voxel within a predetermined periphery in the previous layer. Therefore, the data in the cache space cannot be released directly in this situation. In response to the particle entering the nth layer of the simulation region, based on the voxel parameters of the simulation region and the attribute parameters of the particle, it is determined that the particle does not deposit energy in the mth layer voxel again. Therefore, the cache space corresponds to each voxel in the deposition region corresponding to each voxel in the layers before the mth layer is released. For the predetermined periphery in a layer before the nth layer such as the n−1st layer or the n−2nd layer, the scattering particles, also referred to as secondary particles, of the particles entering the nth layer return to affect the deposition energy in the voxels, and the cache space corresponding to each voxel in the corresponding deposition region of the voxels of each layer between the nth layer and the mth layer is held back from being released, which ensures that the deposition energy generated by the scattered particles can be recorded.

However, in the case that the particles penetrate the simulation region, the particles do not generate deposition energy for the voxels within the simulation region. In this way, the cache space corresponding to each voxel in the deposition region of each voxel in the other layers can be released.

S502, the data stored in the released cache space is transferred to the shared storage space.

In the case that the data in the cache space is released, the data stored in the cache space can be determined as the energy contribution to the corresponding voxels of the particle and/or the secondary particle produced by the particle within the simulation region, and the data can be transferred to the shared storage space.

In the method according to the embodiments of the present disclosure, the cache space corresponding to each voxel in the deposition region corresponding to each voxel in each layer before the mth layer can be released in response to the particle entering the nth layer, and the released data can be transferred into the shared storage space, i.e., the accuracy of the statistical results is ensured, and the flexible utilization of the cache resources is also ensured.

Because the plurality of particles for performing the Monte Carlo simulation in the process for determining the radiotherapy dose are acquired by sampling, the dose determined by the parallel Monte Carlo simulation process for the plurality of particles is bound to have an uncertainty. Therefore, based on the method for determining the radiotherapy dose provided by the above embodiments, the embodiments of the present disclosure also provide a possible implementation for calculating an uncertainty, such that the reliability of the simulation process is evaluated. In the embodiments, the method for determining the radiotherapy dose further includes:

calculating an uncertainty of the parallel Monte Carlo simulation based on the deposition energy of an Nth particle in the shared storage space, wherein N is a quantity of the plurality of particles.

The Nth particle refers to the last particle to release the cache space, and the deposition energy of the Nth particle refers to the deposition energy statistical parameter acquired by counting the deposition energy of each voxel of the Nth particle in the corresponding layer of deposition region sequentially. The sequence of the Nth particle refers to the sequence of releasing the cache and transferring the data into the shared storage space.

In some embodiments, the data stored in the cache space corresponding to each voxel in each layer of deposition region is the deposition energy in each voxel in the deposition region of the corresponding layer of the particle. In the case that the cache space with the data released is the cache space of each voxel of the lth particle in the corresponding layer of deposition region, the deposition energy of each voxel of the lth particle in the corresponding layer deposition region is counted to acquire the deposition energy of the lth particle, and the counted energy in the shared storage space is updated to the deposition energy of the lth particle. That is, the deposition energy of the lth particle in the shared storage space is the deposition energy statistical parameter upon the lth particle being transferred.

In the case that the cache space with data released is the cache space of each voxel of the first particle in the corresponding layer of deposition region, the deposition energy of each voxel of the first particle in the corresponding layer of deposition region is counted to acquire the deposition energy of the first particle, and the counted deposition energy of the first particle is stored into the shared storage space. In the case that the cache space with data released is a cache space of each voxel of a quantity of particles greater than 1 in the corresponding layer of deposition region, the deposition energy is counted again, based on the deposition energy of the stored particles in the shared storage space and the deposition energy of the particles in the currently released cache space of each voxel in the corresponding layer of deposition region, such that the deposition energy of the current particles are acquired and the deposition energy statistics parameter of the shared storage space is updated to the deposition energy of the current particle.

In this way, in the case that 1=N, i.e., the quantity of sampled particles, it is determined that the parallel Monte Carlo simulation for the plurality of particles is finished. In this way, the deposition energy of the Nth particle stored in the shared storage space is the deposition energy of all the sampled particles, and the uncertainty of the parallel Monte Carlo simulation for the plurality of particles is calculated based on the deposition energy of the Nth particle.

In the method provided by the embodiments of the present disclosure, in the case that the deposition energy of the Nth particle is transferred to the shared storage space, that is, in the case that the deposition energy of the last particle among the N particles is available, the uncertainty of the parallel Monte Carlo simulation is calculated based on the deposition energy of the Nth particle. That is, the uncertainty of the parallel Monte Carlo simulation for the plurality of particles is calculated based on the deposition energy of the Nth particle only in the case that the Monte Carlo simulation for all sampled particles is finished. In the process of the Monte Carlo simulation of the particles, it is only necessary to update the counted deposition energy of the new particles based on the cache spaces of the new particles in the released cache spaces of the voxels in the deposition region of the corresponding layer, and based on the updating result, it is possible to update the deposition energy of the particles in the shared storage space without the need to calculate the uncertainty. Therefore, the method provided by the embodiments of the present disclosure is actually a method for calculating the uncertainty by counting the deposition energy of the particles in an online manner, compared with calculating the uncertainty at once upon acquiring all the deposition energy of the particles, the stability of calculating the uncertainty can be effectively improved, the rounding error in the process of calculating the uncertainty is reduced, and the accuracy of the calculation of the uncertainty is ensured.

In addition, in the method provided by the embodiments of the present disclosure, the deposition energy of the particle in the shared storage space refers to the statistical value of the deposition energy of the voxels in the deposition region of the corresponding layer for the particle, such that in the process of the parallel Monte Carlo simulation, the deposition energy of the particle can be counted only, and the corresponding cache region in the shared storage space can be allocated to store the statistical value of the deposition energy. The uncertainty of the parallel Monte Carlo simulation is calculated based on the deposition energy of the particles recorded in the shared storage space only in the case that the parallel Monte Carlo simulation is finished. Therefore, fewer storage resources can be used in the calculation of the uncertainty, i.e., the online real-time counting of the deposition energy is ensured, and the use of fewer storage resources is also ensured.

For the calculation of the uncertainty of the parallel Monte Carlo simulation, embodiments of the present disclosure also provide a possible implementation, calculating the uncertainty of the parallel Monte Carlo simulation based on the deposition energy of the Nth particle in the shared storage space, as shown above, includes:

calculating the uncertainty of the parallel Monte Carlo simulation based on the deposition energy of the Nth particle in a single voxel and an energy variance of the Nth particle in a single voxel.

The deposition energy of the Nth particle in the single voxel is an average deposition dose of the Nth particle in corresponding voxels, and the energy variance of the Nth particle in the single voxel is a sum of a variance of the deposition energy of the Nth particle in corresponding voxels and the average deposition energy.

Exemplarily, the uncertainty of the parallel Monte Carlo simulation is calculated based on the deposition energy of the Nth particle in the single voxel, and the energy variance of the Nth particle in the single voxel by using the following equation (1).

$$\frac{1}{u_N}\sqrt{\frac{S_N}{N-1}}, \quad \text{equation (1)}$$

wherein N is the quantity of sampled particles, i.e., the quantity of the plurality of particles, N is a positive integer greater than 1, $u_N$ is the deposition energy of the Nth particle in a single voxel, and $S_N$ is the energy variance of the kth particle in a single voxel.

In the embodiments, the deposition energy of the Nth particle includes the deposition energy of the Nth particle in a single voxel and energy variance of the Nth particle in a single voxel, i.e., two energy statistical parameters for the Nth particle. Therefore, in the process of parallel Monte Carlo simulation, there are only two storage areas in the shared storage space to store these two energy statistical parameters, and the size of the two storage areas configured to store the two energy statistics can be the same.

The process of updating the deposition energy of the particles in the shared storage space, i.e., the two energy statistics of the particles, in the process of calculating the uncertainty is explained in the following example.

Assuming that the deposition energy of the N−1st particle in a single voxel is $u_{N-1}$, in the case that the released cache space is the cache space of each voxel of the Nth particle in the deposition region of the corresponding layer, an average value of the deposition energy of the Nth particle in each voxel of the corresponding layer can be calculated as the contribution energy $x_N$ of the Nth particle in the voxel, based on the cache space of each voxel of the Nth particle in the corresponding layer of deposition region. The deposition energy $u_N$ of the Nth particle in a single voxel can be acquired by using the following equation (2).

$$u_N = u_{N-1} + \frac{1}{N}(x_N - u_{N-1}), \quad \text{equation (2)}$$

Assuming that the energy variance of the N−1st particle in a single voxel is $S_{N-1}$, $S_{N-1}$ can be expressed as the following equation (3).

$$S_{N-1} = \sum_{i=1}^{N-1}(x_i - u_{N-1})^2, \quad \text{equation (3)}$$

In this way, based on the energy variance $S_{N-1}$ of the Nth particle in a single voxel, the contribution energy $x_N$ of the Nth particle in a single voxel, the deposition energy $u_{N-1}$ of the Nth particle in a voxel, and the deposition energy $u_N$ of the Nth particle in a single voxel, the energy variance of the Nth particle in a single voxel is calculated by using the following equation (4).

$$S_N = S_{N-1} + (x_N - u_{N-1})^2 - \frac{1}{N}(x_N - u_N)^2, \quad \text{equation (4)}$$

In the method provided by the embodiments of the present disclosure, the uncertainty of the parallel Monte Carlo simulation can be calculated based on the deposition energy of the Nth particle in a single voxel, and the energy variance of the Nth particle in a single voxel. Both the deposition energy of the Nth particle in a single voxel and the energy variance of the Nth particle in a single voxel are based on the corresponding energy statistical parameter of a voxel of a previous particle, which effectively ensures the statistical accuracy and stability of the energy statistical parameters, effectively reduces the rounding error in the process of updating the deposition energy, and effectively ensures the accuracy of calculating the uncertainty.

The following describes the apparatus for determining the radiotherapy dose, the device, the storage medium, and the like provided by the present disclosure for implementation, and the specific implementation process and technical effect thereof are described above, which are not repeated hereinafter.

Figure 6:
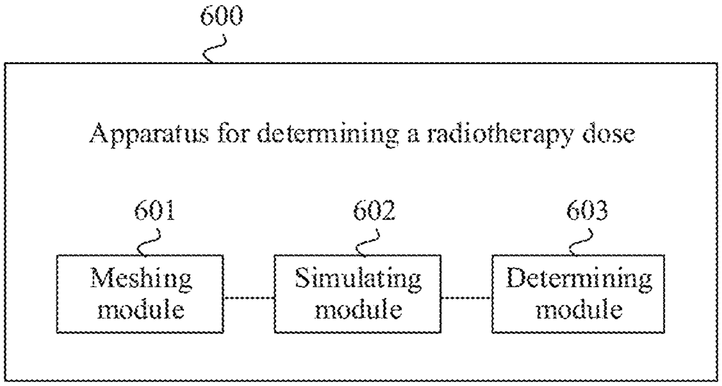
FIG. 6 is a schematic diagram of an apparatus for determining a radiotherapy dose according to some embodiments of the present disclosure.

FIG. 6 is a schematic diagram of an apparatus for determining a radiotherapy dose according to some embodiments of the present disclosure, as shown in FIG. 6, the apparatus for determining the radiotherapy dose includes:

a meshing module 601, configured to acquire a plurality of voxels by performing a three-dimensional meshing on a simulation region;

a simulating module 602, configured to acquire simulation results of a plurality of particles by performing a parallel Monte Carlo simulation on the plurality of particles sampled within the simulation region; and a determining module 603, configured to determine a deposition dose for each of the plurality of voxels based on the simulation results.

Optionally, the simulating module 602, is specifically configured to determine, based on each of the plurality of particles, an incident angle and incident voxels of the corresponding particle entering the simulation region; and acquire, based on the incident angle and the incident voxels, the simulation result by allocating cache spaces for a portion of the voxels within the simulation region and perform a Monte Carlo simulation until the particle penetrates the simulation region, wherein the cache space is configured to store deposition energy of the particle in a corresponding voxel.

Optionally, the simulating module 602 is specifically configured to sequentially determine, based on the incident angle and the incident voxels, a deposition region corresponding to each layer of voxels of the particle in the simulation region; allocate a corresponding cache space for each voxel in the deposition region corresponding to each layer of voxels; perform the Monte Carlo simulation based on the incident angle and the incident voxels until the particle penetrates the simulation region and store the deposition energy of the particle in the corresponding voxel into the cache space; and acquire the simulation result by transferring data in the cache space to a shared storage space.

Optionally, the simulating module 602 is specifically configured to determine, based on the incident angle, the incident voxels and voxels within a predetermined periphery of the incident voxels in a first layer of voxels as a first layer of deposition region corresponding to the particle in the first layer of voxels; allocate a corresponding cache space for each voxel in the first layer of deposition region to store deposition energy of each voxel in the first layer of deposition region; determine, in the case that the particle enters a next layer of voxels, voxels within a region of the next layer of voxels corresponding to the first layer of deposition region and voxels within a predetermined periphery thereof as a second layer of deposition region corresponding to the particle in the next layer of voxels; allocate a corresponding cache space for each voxel in the second layer of deposition region to store deposition energy of each voxel in the second layer of deposition region; and sequentially determine a deposition region when the particle entering each layer of voxels and allocate a corresponding cache space to store deposition energy of each voxel in a corresponding deposition region.

Optionally, the simulating module 602 is specifically configured to release, in response to the particle entering a nth layer of the simulation region, a cache space corresponding to each voxel in a deposition region corresponding to each layer of voxels before a mth layer, wherein m is a positive integer less than n; and transfer data stored in the released cache space to the shared storage space.

Optionally, the apparatus for determining the radiotherapy dose 600 further includes:

a calculating module configured to calculate an uncertainty of a parallel Monte Carlo simulation according to deposition energy of an Nth particle in the shared storage space, wherein N is equal to a quantity of the plurality of particles.

Optionally, the calculating module is specifically configured to calculate the uncertainty of the parallel Monte Carlo simulation according to deposition energy of the Nth particle in a single voxel and an energy variance of the Nth particle in a single voxel.

The deposition energy of the Nth particle in the single voxel is an average deposition dose of the Nth particle in corresponding voxels, and the energy variance of the Nth particle in the single voxel is a sum of a variance of the deposition energy of the Nth particle in corresponding voxels and the average deposition energy.

The apparatus above-mentioned is used for executing the method for determining the radiotherapy dose provided by the above embodiments, and the implementation principle and technical effects are similar, which are not described herein again.

These above modules can be one or more integrated circuits configured to perform the above method, for example, one or more application specific integrated circuits (ASIC), or, one or more digital signal processors (DSP), or one or more field programmable gate arrays (FPGAs), and the like. For example, in the case that one of the above modules is implemented in the form of a processing element scheduling program code, the processing element can be a general-purpose processor, such as a central processing unit (CPU), or other processors that can invoke the program code. For another example, the modules can be integrated and realized in the form of a system-on-a-chip (SOC).

Figure 7:
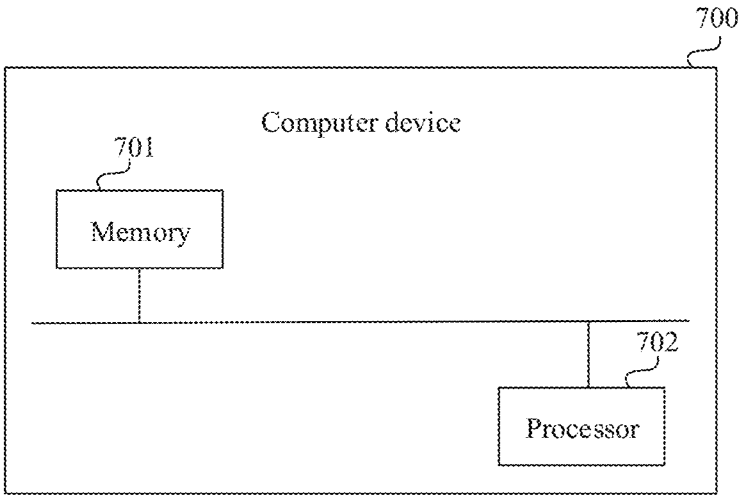
FIG. 7 is a schematic diagram of a computer device according to some embodiments of the present disclosure.

FIG. 7 is a schematic diagram of a computer device according to some embodiments of the present disclosure. As shown in FIG. 7, the computer device 700 includes a memory 701 and a processor 702. The memory 701 and the processor 702 are connected via a bus.

The memory 701 stores one or more computer programs executable by the processor 702, and the processor 702, when loading and executing the one or more computer programs, can be caused to perform the above method embodiments. The specific implementations and technical effects are similar and are not repeated herein.

Based on the above method for determining the radiotherapy dose, the embodiments of the present disclosure also provide a computer-readable storage medium for performing the above method for determining the radiotherapy dose. The computer-readable storage medium may be a non-volatile storage medium having one or more computer programs stored thereon, and the one or more computer programs, when loaded and executed by a processor, causes the processor to perform the above method embodiments.

In the several embodiments provided in the present disclosure, it should be understood that the apparatus and methods disclosed can be realized in other ways. For example, the apparatus embodiments described above are merely schematic, e.g., the division of the elements described, is merely a logical functional division, and the actual implementation can be divided in other ways, e.g., a plurality of elements or components can be combined or integrated into another system, or some of the features can be ignored or not be implemented. In addition, the coupling or direct coupling or communication connection between each other shown or discussed can be an indirect coupling or communication connection through some interface, device, or element, which can be electrical, mechanical, or otherwise.

The elements illustrated as separated components may or may not be physically separated, and components shown as elements may or may not be physical elements, i.e., the elements may be disposed in a single place or may also be distributed over a plurality of network elements. Some or all of these elements may be selected to fulfill the purpose of the embodiment scheme according to actual needs.

In addition, the various functional units in the various embodiments of the present disclosure can be integrated in a single processing element, or the elements can be physically present separately, or two or more elements can be integrated in a single element. The above-integrated elements can be realized either in the form of hardware or in the form of hardware plus software functional elements.

The above-integrated element realized in the form of a software function element can be stored in a computer-readable storage medium. The above software functional element is stored in a storage medium including a plurality of instructions for causing a computer device (which may be a personal computer, a server, or a network device, etc.) or a processor to perform some of the steps of the method described in various embodiments of the present disclosure. The above storage media include USB flash drives, removable hard disks, read-only memory (ROM), random access memory (RAM), magnetic disks or CD-ROMs, and other media that can store program code.

The above is only a specific embodiment of the present disclosure, but the scope of protection of the present disclosure is not limited thereto, and any skilled person familiar with the technical field can easily think of changes or substitutions within the scope of the technology disclosed in the present disclosure, all of which should be covered by the scope of protection of the present disclosure. Therefore, the scope of protection of this application shall be subject to the scope of protection of the claims.

The invention claimed is:

1. A method for determining a radiotherapy dose, comprising:

acquiring a plurality of voxels by performing a three-dimensional meshing on a simulation region;

acquiring simulation results of a plurality of particles by performing a parallel Monte Carlo simulation on the plurality of particles sampled within the simulation region; and determining a deposition dose for each of the plurality of voxels based on the simulation results of the plurality of particles;

wherein said acquiring the simulation results of the plurality of particles by performing the parallel Monte Carlo simulation on the plurality of particles sampled within the simulation region comprises:

determining, based on each of the plurality of particles, an incident angle and incident voxels of the particle entering the simulation region; and acquiring, based on the incident angle and the incident voxels, the simulation result by allocating cache spaces for a portion of the voxels within the simulation region and performing a Monte Carlo simulation until the particle penetrates the simulation region, wherein the cache space is configured to store deposition energy of the particle in a corresponding voxel.

2. The method according to claim 1, wherein said acquiring, based on the incident angle and the incident voxels, the simulation result by allocating the cache spaces for the portion of the voxels within the simulation region and performing the Monte Carlo simulation until the particle penetrates the simulation region comprises:

sequentially determining, based on the incident angle and the incident voxels, a deposition region of the particle corresponding to each layer of voxels within the simulation region;

allocating a cache space for each voxel in the deposition region corresponding to each layer of voxels;

performing the Monte Carlo simulation based on the incident angle and the incident voxels until the particle penetrates the simulation region and storing the deposition energy of the particle in the corresponding voxel into the cache space; and acquiring the simulation result by transferring data in the cache space to a shared storage space.

3. The method according to claim 2, wherein said sequentially determining, based on the incident angle and the incident voxels, the deposition region of the particle corresponding to each layer of voxels within the simulation region, and allocating the corresponding cache space for each voxel in the deposition region corresponding to each layer of voxels comprises:

determining, based on the incident angle, the incident voxels and voxels within a predetermined periphery of the incident voxels in a first layer of voxels as a first layer of deposition region of the particle corresponding to the first layer of voxels;

allocating a corresponding cache space for each voxel in the first layer of deposition region to store deposition energy of each voxel in the first layer of deposition region;

determining, in a case that the particle enters a next layer of voxels, voxels within a region of the next layer of voxels corresponding to the first layer of deposition region and voxels within a predetermined periphery thereof as a second layer of deposition region of the particle corresponding to the next layer of voxels;

allocating a corresponding cache space for each voxel in the second layer of deposition region to store deposition energy of each voxel in the second layer of deposition region; and sequentially determining a deposition region of the particle entering each layer of voxels and allocating a corresponding cache space to store deposition energy of each voxel in a corresponding deposition region.

4. The method according to claim 2, wherein said acquiring the simulation result by transferring the data in the cache space to the shared storage space comprises:

releasing, in response to the particle entering an nth layer of the simulation region, a cache space corresponding to each voxel in a deposition region corresponding to each layer of voxels before an mth layer, wherein m is a positive integer less than n; and transferring data stored in the released cache space to the shared storage space.

5. The method according to claim 4, further comprising:

calculating an uncertainty of the parallel Monte Carlo simulation according to deposition energy of an Nth particle in the shared storage space, wherein N is equal to a quantity of the plurality of particles.

6. The method according to claim 5, wherein said calculating the uncertainty of the parallel Monte Carlo simulation according to the deposition energy of the Nth particle in the shared storage space comprises:

calculating the uncertainty of the parallel Monte Carlo simulation according to deposition energy of the Nth particle in a single voxel and an energy variance of the Nth particle in a single voxel;

wherein the deposition energy of the Nth particle in the single voxel is an average deposition dose of the Nth particle in corresponding voxels, and the energy variance of the Nth particle in the single voxel is a sum of a variance of the deposition energy of the Nth particle in corresponding voxels and an average deposition energy.

7. A non-transitory computer-readable storage medium storing one or more computer programs, wherein the one or more computer programs, when loaded and executed by a processor, cause the processor to perform a method for determining a radiotherapy dose, wherein the method comprises:

acquiring a plurality of voxels by performing a three-dimensional meshing on a simulation region;

acquiring simulation results of a plurality of particles by performing a parallel Monte Carlo simulation on the plurality of particles sampled within the simulation region; and determining a deposition dose for each of the plurality of voxels based on the simulation results of the plurality of particles;

wherein said acquiring the simulation results of the plurality of particles by performing the parallel Monte Carlo simulation on the plurality of particles sampled within the simulation region comprises:

determining, based on each of the plurality of particles, an incident angle and incident voxels of the particle entering the simulation region; and acquiring, based on the incident angle and the incident voxels, the simulation result by allocating cache spaces for a portion of the voxels within the simulation region and performing a Monte Carlo simulation until the particle penetrates the simulation region, wherein the cache space is configured to store deposition energy of the particle in a corresponding voxel.

8. The non-transitory computer-readable storage medium according to claim 7, wherein said acquiring, based on the incident angle and the incident voxels, the simulation result by allocating the cache spaces for the portion of the voxels within the simulation region and performing the Monte Carlo simulation until the particle penetrates the simulation region comprises:

sequentially determining, based on the incident angle and the incident voxels, a deposition region of the particle corresponding to each layer of voxels within the simulation region;

allocating a cache space for each voxel in the deposition region corresponding to each layer of voxels;

performing the Monte Carlo simulation based on the incident angle and the incident voxels until the particle penetrates the simulation region and storing the deposition energy of the particle in the corresponding voxel into the cache space; and acquiring the simulation result by transferring data in the cache space to a shared storage space.

9. The non-transitory computer-readable storage medium according to claim 8, wherein said sequentially determining, based on the incident angle and the incident voxels, the deposition region of the particle corresponding to each layer of voxels within the simulation region, and allocating the corresponding cache space for each voxel in the deposition region corresponding to each layer of voxels comprises:

determining, based on the incident angle, the incident voxels and voxels within a predetermined periphery of the incident voxels in a first layer of voxels as a first layer of deposition region of the particle corresponding to the first layer of voxels;

allocating a corresponding cache space for each voxel in the first layer of deposition region to store deposition energy of each voxel in the first layer of deposition region;

determining, in a case that the particle enters a next layer of voxels, voxels within a region of the next layer of voxels corresponding to the first layer of deposition region and voxels within a predetermined periphery thereof as a second layer of deposition region of the particle corresponding to the next layer of voxels;

allocating a corresponding cache space for each voxel in the second layer of deposition region to store deposition energy of each voxel in the second layer of deposition region; and sequentially determining a deposition region of the particle entering each layer of voxels and allocating a corresponding cache space to store deposition energy of each voxel in a corresponding deposition region.

10. The non-transitory computer-readable storage medium according to claim 8, wherein said acquiring the simulation result by transferring the data in the cache space to the shared storage space comprises:

releasing, in response to the particle entering an nth layer of the simulation region, a cache space corresponding to each voxel in a deposition region corresponding to each layer of voxels before an mth layer, wherein m is a positive integer less than n; and transferring data stored in the released cache space to the shared storage space.

11. The non-transitory computer-readable storage medium according to claim 10, wherein the method further comprises:

calculating an uncertainty of the parallel Monte Carlo simulation according to deposition energy of an Nth particle in the shared storage space, wherein N is equal to a quantity of the plurality of particles.

12. The non-transitory computer-readable storage medium according to claim 11, wherein said calculating the uncertainty of the parallel Monte Carlo simulation according to the deposition energy of the Nth particle in the shared storage space comprises:

calculating the uncertainty of the parallel Monte Carlo simulation according to deposition energy of the Nth particle in a single voxel and an energy variance of the Nth particle in a single voxel;

wherein the deposition energy of the Nth particle in the single voxel is an average deposition dose of the Nth particle in corresponding voxels, and the energy variance of the Nth particle in the single voxel is a sum of a variance of the deposition energy of the Nth particle in corresponding voxels and an average deposition energy.

13. A computer device, comprising a memory and a processor, wherein the memory stores one or more computer programs executable by the processor, and the processor, when loading and executing the one or more computer programs, is caused to perform a method for determining a radiotherapy dose, wherein the method includes:

acquiring a plurality of voxels by performing a three-dimensional meshing on a simulation region;

acquiring simulation results of a plurality of particles by performing a parallel Monte Carlo simulation on the plurality of particles sampled within the simulation region; and determining a deposition dose for each of the plurality of voxels based on the simulation results of the plurality of particles;

wherein said acquiring the simulation results of the plurality of particles by performing the parallel Monte Carlo simulation on the plurality of particles sampled within the simulation region comprises:

determining, based on each of the plurality of particles, an incident angle and incident voxels of the particle entering the simulation region; and acquiring, based on the incident angle and the incident voxels, the simulation result by allocating cache spaces for a portion of the voxels within the simulation region and performing a Monte Carlo simulation until the particle penetrates the simulation region, wherein the cache space is configured to store deposition energy of the particle in a corresponding voxel.

14. The computer device according to claim 13, wherein said acquiring, based on the incident angle and the incident voxels, the simulation result by allocating the cache spaces for the portion of the voxels within the simulation region and performing the Monte Carlo simulation until the particle penetrates the simulation region comprises:

sequentially determining, based on the incident angle and the incident voxels, a deposition region of the particle corresponding to each layer of voxels within the simulation region;

allocating a cache space for each voxel in the deposition region corresponding to each layer of voxels;

performing the Monte Carlo simulation based on the incident angle and the incident voxels until the particle penetrates the simulation region and storing the deposition energy of the particle in the corresponding voxel into the cache space; and acquiring the simulation result by transferring data in the cache space to a shared storage space.

15. The computer device according to claim 14, wherein said sequentially determining, based on the incident angle and the incident voxels, the deposition region of the particle corresponding to each layer of voxels within the simulation region, and allocating the corresponding cache space for each voxel in the deposition region corresponding to each layer of voxels comprises:

determining, based on the incident angle, the incident voxels and voxels within a predetermined periphery of the incident voxels in a first layer of voxels as a first layer of deposition region of the particle corresponding to the first layer of voxels;

allocating a corresponding cache space for each voxel in the first layer of deposition region to store deposition energy of each voxel in the first layer of deposition region;

determining, in a case that the particle enters a next layer of voxels, voxels within a region of the next layer of voxels corresponding to the first layer of deposition region and voxels within a predetermined periphery thereof as a second layer of deposition region of the particle corresponding to the next layer of voxels;

allocating a corresponding cache space for each voxel in the second layer of deposition region to store deposition energy of each voxel in the second layer of deposition region; and sequentially determining a deposition region of the particle entering each layer of voxels and allocating a corresponding cache space to store deposition energy of each voxel in a corresponding deposition region.

16. The computer device according to claim 14, wherein said acquiring the simulation result by transferring the data in the cache space to the shared storage space comprises:

releasing, in response to the particle entering an nth layer of the simulation region, a cache space corresponding to each voxel in a deposition region corresponding to each layer of voxels before an mth layer, wherein m is a positive integer less than n; and transferring data stored in the released cache space to the shared storage space.

17. The computer device according to claim 16, wherein the method further comprises:

calculating an uncertainty of the parallel Monte Carlo simulation according to deposition energy of an Nth particle in the shared storage space, wherein N is equal to a quantity of the plurality of particles.

* * * * *